(12) United States Patent
Dunkley et al.

(10) Patent No.: US 8,293,630 B2
(45) Date of Patent: Oct. 23, 2012

(54) MATERIAL AND METHOD OF FABRICATION THEREFOR

(75) Inventors: John Joseph Dunkley, Meadowhall (GB); Brett Telford, Meadowhall (GB); Stephen Edward Connor, Malvern (GB)

(73) Assignee: Psimedica Limited, Malvern (GB)

( * ) Notice: Subject to any disclaimer, the term of this patent is extended or adjusted under 35 U.S.C. 154(b) by 1372 days.

(21) Appl. No.: 10/585,324

(22) PCT Filed: Dec. 15, 2004

(86) PCT No.: PCT/GB2004/005243
§ 371 (c)(1),
(2), (4) Date: Sep. 26, 2006

(87) PCT Pub. No.: WO2005/066073
PCT Pub. Date: Jul. 21, 2005

(65) Prior Publication Data
US 2007/0190761 A1   Aug. 16, 2007

(30) Foreign Application Priority Data
Jan. 6, 2004   (GB) .................................. 0400149.1

(51) Int. Cl.
*H01L 21/22*   (2006.01)
*H01L 21/38*   (2006.01)

(52) U.S. Cl. ..................................... 438/544; 250/492.3

(58) Field of Classification Search .................. 424/1.11; 250/492.3; 438/544
See application file for complete search history.

(56) References Cited

U.S. PATENT DOCUMENTS

| | | |
|---|---|---|
| 4,789,596 A | 12/1988 | Allen et al. |
| 5,094,832 A | 3/1992 | Forwald et al. |
| 5,302,369 A | 4/1994 | Day et al. |
| 5,894,133 A | 4/1999 | Armini |
| 5,926,727 A | 7/1999 | Stevens et al. |
| 2004/0091421 A1 * | 5/2004 | Aston et al. .................. 424/1.11 |

FOREIGN PATENT DOCUMENTS

| | | |
|---|---|---|
| EP | 1 211 223 A1 | 6/2002 |
| JP | 2-9705 | 1/1990 |
| JP | 7211665 * | 8/1995 |
| JP | 7211665 A | 8/1995 |
| JP | 11-510469 | 9/1999 |
| WO | WO 97/06101 | 2/1997 |
| WO | 98/27246 A | 6/1998 |
| WO | 02/067998 A2 | 9/2002 |

OTHER PUBLICATIONS

Properties of Porous Silicon, edited by Leigh Canhan, DERA, Malvern, UK, Published by INSPEC, The Institution of Electrical Engineers, London, United Kingdom, ISBN 085296 932 5, Halimaoui, "1.2 Porous Silicon Formation by Anodisation", pp. 12-19; 1997.
International Search Report for PCT/GB2004/005243 dated Mar. 30, 2005.
Properties of Porous Silicon, EMIS Datareviews Series 18, Institute of Electrical Engineers, ISBN 085296 932 5, pp. 12-19, 1997.

* cited by examiner

*Primary Examiner* — Michael G Hartley
*Assistant Examiner* — Jagadishwar Samala
(74) *Attorney, Agent, or Firm* — Nixon & Vanderhye P.C.

(57) ABSTRACT

The present invention concerns new methods of fabricating a silicon material comprising phosphorus. The methods allow high levels of phosphorus to be combined with the silicon. In one aspect of the invention a sample of phosphorus is surrounded with a sample of silicon. At least some of the phosphorus is then vaporised and caused to interact with the silicon.

8 Claims, 1 Drawing Sheet

MATERIAL AND METHOD OF FABRICATION THEREFOR

Figure 1:
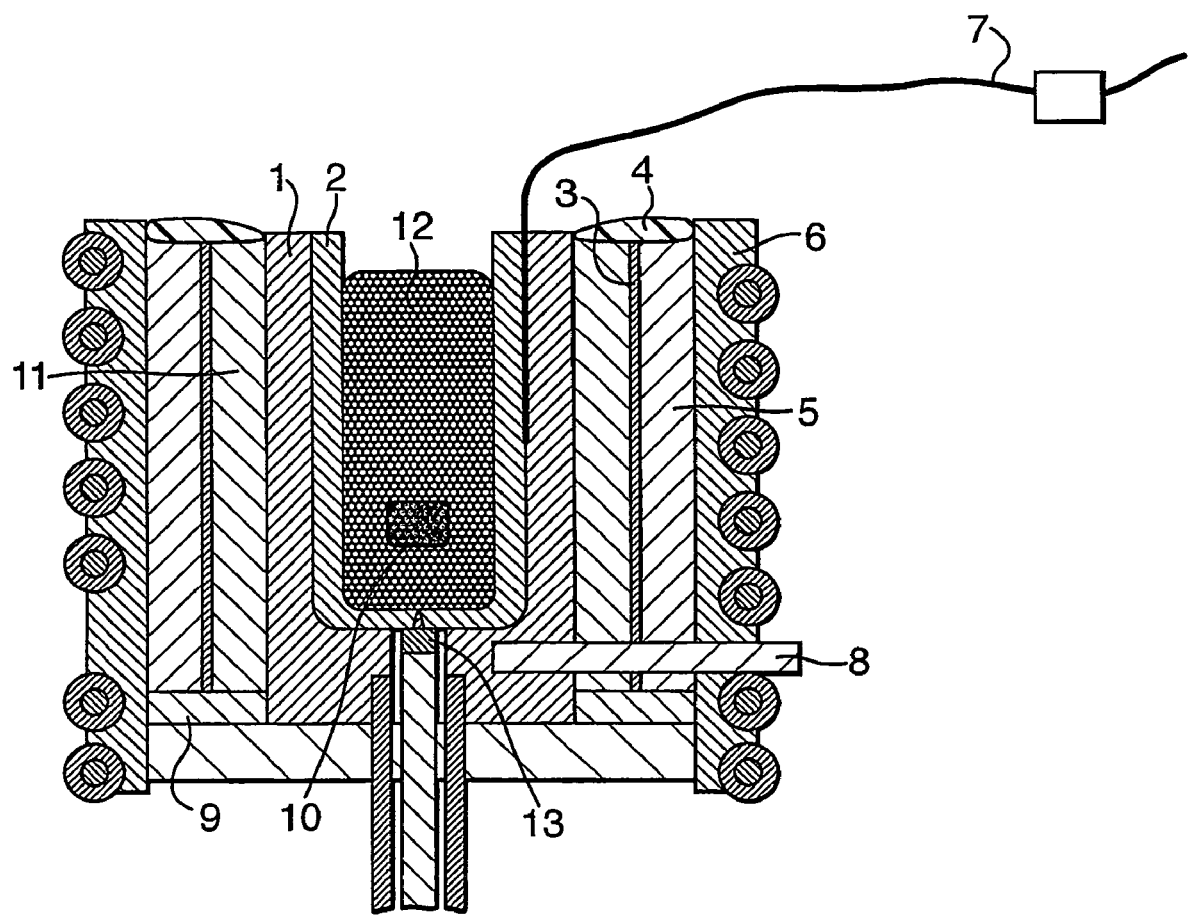

This application is the U.S. national phase of international application PCT/GB2004/005243 filed Dec. 15, 2004 which designated the U.S. and claims benefit of GB 0400149.1, filed 6 Jan. 2004, the entire contents of each of which are hereby incorporated by reference.

The present invention relates to a new composite material and a new method of fabricating a composite material. More specifically the present invention relates to a new composite material comprising silicon and phosphorus, and to a new method for combining silicon and phosphorus.

The introduction of impurity atoms into silicon typically forms a significant part of the process for fabricating silicon integrated circuits. The most commonly used methods of introducing dopants into silicon are: (a) by diffusion of the impurity into the silicon from a source that is spatially separate from the silicon, (b) diffusion from an oxide layer that has been formed on the surface of the silicon, and (c) ion implantation of the silicon followed by diffusion and annealing.

Phosphorus is commonly used as a dopant for semiconductor junction formation. For diffusion of phosphorus into silicon from a $POCl_3$ source, diffusion temperatures between 890 C and 1050 C are typically required. Diffusion of phosphorus from $PBr_3$ and other sources is also possible.

The introduction of dopants into silicon by ion implantation may be achieved by vaporising a source of the dopant atoms, causing the atoms to be charged, accelerating the ions formed from the atoms, and directing the ions to the silicon substrate. Disruption of the silicon lattice as a result of interaction with the ions may be removed by subsequent heat treatment. In this way phosphorus may be introduced into the silicon at concentrations of $10^{20}$ $cm^{-3}$. Ion implantation may be used to modify the concentration of a dopant in a thin surface layer of silicon, the silicon layer thickness typically being less than one micron.

Silicon alloys have been fabricated by melting silicon with certain elements, the molten alloy then being cast in the form of a block. Silicon powder may be formed by crushing such blocks. However, the non-silicon elements, present in alloys formed in this way, often tend to segregate during casting. This means that powders formed from such blocks will be inhomogeneous as a result of this segregation.

Pure silicon has a relatively high melting point (1420 C) and this makes it difficult to combine molten silicon with elements that have a low boiling points. For example, red phosphorus has a boiling point of 417 C, so that when red phosphorus is bought into contact with molten silicon it vaporises, making it difficult to contain the phosphorus and to combine it with the silicon.

U.S. Pat. No. 5,926,727 provides background information that is relevant to the present invention. The document describes a method of introducing phosphorus into a semiconductor. The method involves the preparation of an ammonium phosphate aqueous solution; semiconductor particles are placed in the ammonium phosphate solution to coat the particle with ammonium phosphate. The coated particle is then dried, and the phosphorus is then allowed or caused to diffuse into the silicon. The diffusion process is typically performed at 950 C.

U.S. Pat. No. 5,094,832 also contains background information that is relevant to the present invention. It describes the gas atomisation of molten silicon. The particle sizes resulting from this type of atomisation are between 0.1 microns and 1000 microns. Phosphorus is present in the silicon particles in amounts between 0 and 0.5%. However, the phosphorus is one of a number of impurities such as sodium, lithium, potassium, magnesium, strontium, barium, and beryllium. Atomisation is achieved by using a stream of inert gas that breaks the flow of the molten silicon, to form small droplets of silicon which cool and solidify.

Substances comprising silicon and phosphorus have also been found to be of value in the treatment of cancer. Such silicon containing substances are described in WO 02/067998 A2.

Cancer can be treated by a number of different methods. One of these methods is radiotherapy, in which the tumour is exposed to gamma or beta radiation. The source of the radiation may be external to the body of the patient, or may be located within the body.

In some cases the source of radiation may be located in the region of the tumour; this type of therapy is known as brachytherapy. By locating the source in the region of the tumour, and by an appropriate choice of radiation source, it is possible to expose the tumour to radiation with relatively minor exposure to healthy tissue.

WO 02/067998 describes the use of several radionucleotides, including $^{32}P$, which is a beta emitter.

It is an objective of the present invention to provide a new composite material comprising silicon and phosphorus, the new composite material being in the form of a powder having substantially uniform chemical composition and having high concentrations of phosphorus. It is a further objective of the invention to provide a new composite material comprising silicon and phosphorus, the new composite material being in the form of a powder having low impurity levels and high concentrations of phosphorus. It is a yet further objective of the invention to provide a new method for fabricating a solid composite material comprising silicon and high concentrations of phosphorus, the method allowing the large scale conversion of silicon to the material.

According to one aspect, the invention provides a method for producing a composite material comprising silicon and phosphorus, the method comprising the steps:
(ai) heating at least part of a sample of silicon to a silicon reaction temperature between 900 C and 1500 C;
(bi) heating at least part of a sample of phosphorus in such a manner that phosphorus vapour is generated and in such a manner that at least part of the sample of phosphorus is heated to a phosphorus vaporisation temperature between 100 C and 800 C; and
(ci) allowing and/or causing at least some of the phosphorus vapour to contact at least part of the sample of silicon that has been heated to the silicon reaction temperature;
wherein steps (ai), (bi), and (ci) are performed in such a manner that a molten composite material comprising the silicon and phosphorus is formed.

Preferably step (ai) comprises the step of heating at least part of the sample of silicon to a silicon reaction temperature between 1000 C and 1250 C and step (bi) comprises the step of heating at least part of the sample of phosphorus to a phosphorus vaporisation temperature between 380 C and 700 C. More preferably step (ai) comprises the step of heating at least part of the sample of silicon to a silicon reaction temperature between 1100 C and 1200 C and step (bi) comprises the step of heating at least part of the sample of phosphorus to a phosphorus vaporisation temperature between 400 C and 450 C.

The step (ai) may comprise the step of heating at least part of the sample of silicon to a reaction temperature of 1131 C±30 C.

The step (bi) may comprise the step of heating at least part of the sample of phosphorus to a phosphorus vaporisation temperature of 417 C±10 C.

The step (ci) may comprise the step of allowing and/or causing between 80% and 100% of the phosphorus sample to contact at least part of the silicon.

The step (ci) may comprise the step of allowing and/or causing between 80% and 99% of the phosphorus sample to contact at least part of the silicon.

The step (ci) may comprise the step of allowing and/or causing between 80% and 95% of the phosphorus sample to contact at least part of the silicon.

Each of steps (ai), (bi), and (ci) may be performed at a pressure of between 700 mm Hg and 800 mm Hg.

The step (ai) of heating the silicon may be initiated before the step (bi) of heating the phosphorus is initiated.

During the method there may be intervals when only part of the sample of silicon is being heated to the silicon reaction temperature, and when only part of the phosphorus is being vaporised.

The method may comprise a further step of heating the molten composite material to temperature above the silicon reaction temperature. The method may comprise a further step of cooling the molten composite material until it is solid.

Increasing the temperature of the composite material above the silicon reaction temperature for an interval, once a substantial proportion (for example 80% or more) of the phosphorus has been converted, may improve the homogeneity of the composite material.

The sample of silicon may have a mass between 1 g and 100 Kg, the sample of phosphorus may have a mass between 1 g and 100 Kg.

The sample of silicon may have a mass between 1 Kg and 100 Kg, the sample of phosphorus may have a mass between 100 g and 10 Kg.

By heating at least part of the silicon to a temperature in the region of 1131 C, which is less than the silicon melting temperature (1420 C), and bringing the phosphorus vapour into contact with the silicon, it is believed that silicon phosphide is formed. Silicon phosphide has a liquid phase at 1131 C and the liquid silicon phosphide is believed to absorb phosphorus vapour more efficiently than solid silicon. It is thought that the silicon phosphide allows the efficient conversion of the silicon and phosphorus by reducing loss of the phosphorus vapour. The fact that the temperature of the silicon is in the region of 1131 C, which is lower than the melting temperature of silicon helps to reduce the rate of phosphorus vaporisation and hence loss of phosphorus before it can combine with the silicon.

By maintaining a temperature difference between the silicon and the phosphorus, it is possible, at least initially, to heat only part of the phosphorus to a temperature in the region of its boiling temperature (417 C). In this way a relatively gradual release of phosphorus vapour may be achieved. If all the solid phosphorus were heated to the silicon reaction temperature, then formation of phosphorus vapour would be very rapid, resulting in loss before it can be converted.

Advantageously the step (ai) comprises the step of using a heat source to heat at least part of the silicon sample and the step (bi) comprises the step of using the same heat source to heat at least part of the phosphorus sample. More advantageously at least some of the silicon is arranged such that it thermally insulates the phosphorus from the heat source.

The use of silicon as a thermal insulator is advantageous since silicon has a relatively low thermal conductivity at the temperatures in question, and allows a temperature difference to be established between the phosphorus and the silicon.

The heat source may be a furnace comprising a melter. The melter may comprise quartz. The melter may comprise alumina.

It is believed that the use of furnace components comprising high purity quartz allows the formation of a silicon alloy comprising phosphorus with minimal contamination from metallic elements.

Preferably the step (ci) comprises the step of substantially enclosing the at least part of the sample of phosphorus with at least part of the sample of silicon so that at least part of the phosphorus vapour formed is caused and/or allowed to pass into and/or onto and/or through at least part of the silicon sample.

Preferably the silicon sample comprises a multiplicity of silicon particles. More preferably the mean size of the silicon sample is between 0.5 and 5 mm.

Some of the silicon particles may be formed into a bed upon which the sample of phosphorus may be placed. The sample of phosphorus may then be blanketed in a further quantity of silicon particles so it is substantially enclosed by a layer of silicon. The use of silicon particles therefore provides a convenient way of enclosing the sample of phosphorus.

Step (ai) may comprise the step of adding silicon particles to a region occupied by at least some of the phosphorus vapour. More preferably step (ai) comprises the step of adding silicon particles to a region occupied by at least some of the phosphorus vapour and by part of the sample of silicon that has been heated to the silicon reaction temperature. Yet more preferably the step (ai) comprises the step of adding silicon particles to a region occupied by at least some of the phosphorus vapour and by a layer of silicon surrounding at least part of the sample of phosphorus.

If the sample of phosphorus is surrounded by a layer of silicon, it is possible that not all the phosphorus vapour will be captured by the silicon layer before it escapes. By adding silicon particles to the region occupied by the phosphorus vapour, some of the silicon particles may react with part of the phosphorus vapour, thereby preventing its escape. The use of silicon particles is advantageous because they have a small mass and so can be rapidly heated to the silicon reaction temperature; the use is also advantageous because the particles have a relatively high surface area.

Advantageously the silicon sample comprises polycrystalline silicon. More advantageously the silicon sample comprises solar grade polycrystalline silicon. Yet more advantageously the silicon sample comprises electronics grade polycrystalline silicon.

More advantageously the sample of phosphorus has a purity of greater or equal to 99.99% measured by mass. Yet more advantageously the sample of phosphorus has a purity of greater or equal to 99.9999% measured by mass.

The sample of phosphorus may comprise white phosphorus.

There are several forms of phosphorus including red phosphorus, white phosphorus, and black phosphorus. White phosphorus is a solid comprising tetrahedral $P_4$ molecules. White phosphorus is thermodynamically less stable than other solid phases under normal conditions. It has a density of 1.8 g cm$^{-3}$ and boiling point of 280 C.

Advantageously the sample of phosphorus comprises red phosphorus.

Red phosphorus may be obtained by heating white phosphorus at 300 C in an inert atmosphere for several days. It is normally obtained as an amorphous solid, but crystalline materials may be prepared having very complex three dimensional network structures. It has a density of 2.2 g cm$^{-3}$ and a boiling point of 417 C.

The use of red phosphorus is advantageous since it is generally less reactive and less volatile than white phosphorus.

The sample of phosphorus may comprise black phosphorus.

When red phosphorus is heated under high pressure, a series of phases of black phosphorus are formed. One of these phases consists of puckered layers having pyramidal three coordinated P atoms.

The sample of silicon may have a purity of greater or equal to 99.99% measured by mass. The sample of silicon may have a purity of greater or equal to 99.99999% measured by mass.

Advantageously the method comprises the further step (di) of atomising the molten composite material generated by step (ci).

The step (di) may comprise the step of gas atomising the molten composite material generated by step (ci). The step (di) may comprise the step of liquid atomising the molten composite material generated by step (ci). The step (di) may comprise the step of water atomising the molten composite material generated by step (ci). The step (di) may comprise the step of cooling the atomised molten composite material.

The steps (ai), (bi), (ci) and (di) may be performed in such a manner that the composite material comprises a powder having a mean particle size between 0.1 microns and 300 microns.

The steps (ai), (bi), (ci), and (di) may be performed in such a manner that the composite material comprises a powder having a mean particle size between 0.1 microns and 100 microns.

The steps (ai), (bi), (ci), and (di) may be performed in such a manner that the composite material comprises a powder, the powder having a multiplicity of uniform composition particles, each uniform composition particle having a substantially uniform chemical composition.

Certain forms of porous and polycrystalline silicon have favourable biological properties, and these properties are described in PCT/GB96/01863. For example porous silicon and polycrystalline silicon have resorbable and bioactive forms.

The steps (ai), (bi), (ci) and (di) may be performed in such a manner that a powder comprising polycrystalline silicon and phosphorus is formed.

Silicon and materials comprising silicon may be porosified by a number of techniques including stain etch techniques and anodisation techniques described in "Properties of Porous Silicon" EMIS Datareviews Series 18, Institute of Electrical Engineers, ISBN 085296 932 5, pages 12 to 29, which is herein incorporated by reference.

The method may comprise the further step of anodising the composite material comprising silicon and phosphorus. The method may comprise the further step (ei) of stain etching the composite material comprising silicon and phosphorus. The step (ei) may be performed after the step (di).

The porosification of the composite material in this way may allow its use for biological applications, for example the porosification may allow the use of the composite material in the formation of silicon implants.

Preferably the step (bi) comprises the step of heating at least part of the sample of phosphorus in a furnace.

According to a further aspect, the invention provides a method for producing a composite material comprising phosphorus and silicon, the method comprising the steps:
(aii) taking a sample of phosphorus;
(bii) substantially surrounding the sample of phosphorus with a layer of silicon;
(cii) applying heat to the silicon in such a manner that a temperature difference is established between at least part of the silicon layer and the sample of phosphorus, and in such a manner that at least some of the phosphorus is vaporised; and
(dii) allowing and/or causing at least some of the phosphorus vapour to contact at least part of the layer of silicon in such a manner that a molten composite material comprising silicon and phosphorus is formed.

The layer of silicon may comprise a layer of silicon particles. The layer of silicon may comprise a layer of silicon particles, each silicon particle comprising polycrystalline silicon.

Preferably steps (aii), (bii), and (cii) are performed in such a manner that at least part of the silicon layer is heated to a silicon reaction temperature between 900 C and 1500 C. More preferably steps (aii), (bii), and (cii) are performed in such a manner that at least part of the layer of silicon is heated to a silicon reaction temperature between 900 C and 1500 C and such that at least part of the phosphorus is heated to a phosphorus vaporisation temperature between 100 C and 1000 C.

Steps (aii), (bii), and (cii) may be performed in such a manner that at least part of the silicon layer is heated to a silicon reaction temperature greater or equal to 1131 C.

Advantageously the silicon reaction temperature is between 1000 C and 1250 C and the phosphorus vaporisation temperature is between 380 C and 500 C. More advantageously the silicon reaction temperature is between 1050 C and 1200 C and the phosphorus vaporisation temperature is between 400 C and 450 C. Yet more advantageously the silicon reaction temperature is between 1100 C and 1150 C and the phosphorus vaporisation temperature is between 400 C and 450 C. Even more advantageously the silicon reaction temperature is 1131 C±5 C and the phosphorus vaporisation temperature is 417 C±5 C.

Steps (cii) and (dii) may both be performed at a pressure of between 700 mm Hg and 800 mm Hg.

The sample of silicon may have a mass between 1 g and 100 Kg, the sample of phosphorus may have a mass between 1 g and 100 Kg.

The sample of silicon may have a mass between 1 Kg and 100 Kg, the sample of phosphorus may have a mass between 100 g and 10 Kg.

Step (cii) may be performed by heating at least part of the silicon layer in a furnace comprising a melter. The melter may comprise quartz. The melter may comprise alumina.

It is believed that the use of furnace components comprising high purity quartz allows the formation of a composite material comprising phosphorus and silicon with minimal contamination from such elements as chromium, cobalt, manganese, cerium, silver, sodium, lithium, potassium, magnesium, strontium, barium, and beryllium.

Advantageously the silicon sample comprises polycrystalline silicon. More Advantageously the silicon sample comprises solar grade polycrystalline silicon. Yet more advantageously the silicon sample comprises electronics grade polycrystalline silicon.

Preferably the silicon sample comprises a multiplicity of silicon particles. More preferably the mean size of the silicon sample is between 0.5 and 5 mm.

Advantageously the sample of phosphorus comprises red phosphorus.

Advantageously the method comprises the further step (eii) of atomising the molten composite material generated by step (dii).

The step (eii) may comprise the step of gas atomising the molten composite material generated by step (dii). The step (eii) may comprise the step of liquid atomising the molten composite material generated by step (dii). The step (eii) may comprise the step of water atomising the molten composite material generated by step (dii). The step (eii) may comprise the step of cooling the atomised molten composite material.

The steps (aii), (bii), (cii), (dii), and (eii) may be performed in such a manner that a powder comprising silicon and phosphorus is formed, and in such a manner that the powder comprises a multiplicity of uniform composition particles, each uniform composition particle having chemical composition that is substantially the same as that of the other uniform composition particles.

The method may comprise a further step of cooling the composite material formed by step (dii).

The method may comprise the further step of porosifying the composite material. The method may comprise the further step of anodising the composite material comprising silicon and phosphorus. The method may comprise the further step of stain etching the composite material comprising silicon and phosphorus.

The method may further comprise the step, performed after and/or during step (cii), of adding silicon particles to a region occupied by at least some of the phosphorus vapour.

According to a further aspect, the invention provides a method for producing a composite material comprising silicon and phosphorus, the method comprising the steps:
(aiii) combining a first sample of solid silicon with a first sample of phosphorus vapour at a temperature and pressure such that liquid silicon phosphide is formed; and
(biii) allowing and/or causing the liquid silicon phosphide to combine with a second sample of silicon and/or a second sample of phosphorus so that a composite material comprising silicon and phosphorus is formed.

For the purposes of this specification, silicon phosphide is a compound having the chemical formula SiP.

The step (aiii) may comprise the step of combining the first sample of solid silicon with a first sample of phosphorus vapour at a temperature between 1000 C and 1250 C. The step (aiii) may comprise the step of combining the first sample of solid silicon with a first sample of phosphorus vapour at a temperature of 1131 C±5 C.

The method may comprise the further step (ciii) of atomising the composite material generated by step (biii).

The steps (aiii), (biii), and (ciii) may be performed in such a manner that a powder comprising silicon and phosphorus is formed, and in such a manner that the powder comprises a multiplicity of uniform composition particles, each uniform composition particle having a chemical composition that is substantially the same as the other uniform composition particles.

The steps (aiii), (biii), and (ciii) may be performed in such a manner that the composite material comprises polycrystalline silicon.

The method may comprise a further step of cooling the composite material formed by step (biii).

The method may comprise the further step of porosifying the composite material. The method may comprise the further step of anodising the composite material comprising silicon and phosphorus. The method may comprise the further step of stain etching the composite material comprising silicon and phosphorus.

The method may further comprise the step of adding silicon particles to a region occupied by at least some of the phosphorus vapour.

According to a further aspect the invention provides a method for producing a composite material comprising silicon and phosphorus, the method comprising the steps:
(aiv) locating a first sample of silicon between a heat source and a sample of phosphorus, so that the sample of phosphorus is insulated from the heat source by the first sample of silicon;
(biv) heating at least part of a sample of phosphorus, using the heat source, so that at least part of the sample of phosphorus is vaporised;
(civ) combining at least part of the phosphorus vapour with at least part of the first sample of silicon and/or with a second sample of silicon so that a molten composite material comprising silicon and phosphorus is formed.

The step (civ) may be performed at a temperature between 1000 C and 1250 C. The step (civ) may be performed at a temperature of 1131 C±20 C.

The method may comprise the further step (div) of atomising the composite material generated by step (civ).

The steps (aiv), (biv), (civ), and (div) may be performed in such a manner that a powder comprising silicon and phosphorus is formed, and in such a manner that the powder comprises a multiplicity of uniform composition particles, each uniform composition particle having a chemical composition that is substantially the same as the other uniform composition particles.

The steps (aiv), (biv), (civ), and (div) may be performed in such a manner that the composite material comprises polycrystalline silicon.

The method may comprise a further step of cooling the composite material formed by step (civ).

The method may comprise the further step of porosifying the composite material. The method may comprise the further step of anodising the composite material comprising silicon and phosphorus. The method may comprise the further step of stain etching the composite material comprising silicon and phosphorus.

The method may further comprise the step of adding silicon particles to a region occupied by at least some of the phosphorus vapour.

According to a further aspect the invention provides a method for producing a composite material comprising silicon and phosphorus, the method comprising the steps:
(av) causing at least part of a sample of phosphrous to vaporise; and
(bv) adding a plurality of particles of phosphorus to a region in which at least part of the phosphorus vapour is located; and
(cv) heating the silicon particles to a temperature between 900 C and 1500 C so that a molten composite material comprising silicon and phosphorus is formed.

The step (cv) may be performed at a temperature between 1000 C and 1250 C. The step (cv) may be performed at a temperature of 1131 C±20 C.

The method may comprise the further step (dv) of atomising the molten composite material generated by step (cv).

The steps (av), (bv), (cv), and (dv) may be performed in such a manner that a powder comprising silicon and phosphorus is formed, and in such a manner that the powder comprises a multiplicity of uniform composition particles, each uniform composition particle having a chemical composition that is substantially the same as the other uniform composition particles.

The steps (av), (bv), (cv), and (dv) may be performed in such a manner that the composite material comprises polycrystalline silicon.

The method may comprise a further step of cooling the composite material formed by step (cv).

The method may comprise the further step of porosifying the composite material. The method may comprise the further step of anodising the composite material comprising silicon and phosphorus. The method may comprise the further step of stain etching the composite material comprising silicon and phosphorus.

The method may further comprise the step of adding silicon particles to a region occupied by at least some of the phosphorus vapour.

According to a further aspect the invention provides a composite material, comprising silicon and phosphorus, obtainable by a method according to any of the above aspects.

According to a further aspect, the invention provides a composite material comprising silicon and phosphorus, the composite material comprising 0.001 and 30 atomic percent of phosphorus.

The composite material may comprise between 1 and 15 atomic percent phosphorus. The composite material may comprise between 1.5 and 15 atomic percent phosphorus. The composite material may comprise between 1.5 and 10 atomic percent phosphorus. The composite material may comprise between 2 and 10 atomic percent phosphorus. The composite material may comprise between 1.5 and 5 atomic percent phosphorus. The composite material may comprise between 2 and 5 atomic percent phosphorus. The composite material may comprise between 3 and 10 atomic percent phosphorus.

The composite material may comprise between 99 and 85 atomic percent silicon. The composite material may comprise between 98.5 and 85 atomic percent silicon. The composite material may comprise between 98.5 and 90 atomic percent silicon. The composite material may comprise between 98 and 90 atomic percent silicon. The composite material may comprise between 98.5 and 95 atomic percent silicon. The composite material may comprise between 98 and 95 atomic percent silicon. The composite material may comprise between 97 and 90 atomic percent silicon.

For the purposes of this specification, a sample of a material comprises an element that is present at x atomic percent, then there are x atoms of the element for every 100 atoms of the material.

The composite material may comprise between 90% and 100%, by mass, of silicon and phosphorus. The composite material may comprise between 99% and 100%, by mass, of silicon and phosphorus. The composite material may comprise between 99.9% and 100%, by mass, of silicon and phosphorus. The composite material may comprise between 99.99% and 100%, by mass, of silicon and phosphorus. The composite material may substantially completely consist of silicon and phosphorus.

The composite material may comprise a powder, the powder having a multiplicity of uniform composition particles, each uniform composition particle having substantially the same chemical composition as the other uniform composition particles.

The composite material may comprise a multiplicity of uniform composition particles and may have a mean particle size between 0.1 microns and 500 microns.

The composite material may comprise one or more of: porous silicon, polycrystalline silicon, bulk crystalline silicon, amorphous silicon, resorbable silicon, bioactive silicon, and biocompatible silicon.

For the purposes of this specification, resorbable silicon is silicon that is capable of erosion when placed in at least one physiological environment; bioactive silicon is silicon that is capable of forming a bond, when implanted in a subject, with human or animal tissue; and biocompatible silicon that is biologically acceptable for specific applications, for example biocompatible silicon has been found to be biologically acceptable for the purposes of anti-cancer treatment.

The phosphorus, from which the composite material is partly formed, may comprise $^{32}P$.

The composite material may comprise $^{32}P$ having, the $^{32}P$ being present at a concentration such that the activity of the composite material is between 0.1 to 50 GBq levels per gram. The composite material may comprise $^{32}P$, the $^{32}P$ being present at a concentration such that the activity of the composite material is between 0.5 to 20 GBq levels per gram. The composite material may comprise $^{32}P$, the $^{32}P$ being present at a concentration such that the activity of the composite material is between 2.5 to 10 GBq levels per gram.

Composite material comprising $^{32}P$ may be used for radiotherapeutic applications. It is believed that the energy of the beta particles emitted from $^{32}P$, and the half life of the $^{32}P$, make it particularly suitable for the treatment of cancer by brachytherapy.

The composite material may comprise less than 0.1 atomic percent of a metallic element. The composite material may comprise less than 0.1 atomic percent of one or more of the following: chromium, cobalt, manganese, cerium, silver, sodium, lithium, potassium, magnesium, strontium, barium, and beryllium.

One method by which a composite material comprising $^{32}P$ may be formed is by neutron transmutation of a composite material comprising $^{31}P$ The presence of impurities such as metallic elements in the composite material may result in the formation of radionucleotides that are less useful for radiotherapeutic applications. Therefore the absence of impurities in the composite material may be advantageous.

For the absence of doubt $^{32}S$, which is one of the decay products of $^{32}P$, is not a metallic element. The composite material may comprise greater than 0.1 atomic percent sulphur.

Preferably the composite material comprises a plurality of uniform composition microparticles, each uniform composition particle comprising between 0.5 and 20 atomic percent P.

The composite material may comprise a powder, the mean particle size of the powder being between 0.1 and 500 microns.

According to a further aspect the invention provides a composition comprising a composite material, comprising silicon and phosphorus, as described in any of the above aspects and an excipient.

The excipient may comprise a liquid. The excipient may comprise an oil. The excipient may be a parentheral excipient. The excipient may comprise one or more of: peanut oil, sesame seed oil, a microcellulose compound, a polyethylene glycol derivative, and a TWEEN additive.

The composite material may comprise $^{32}P$ and a multiplicity of microparticles, at least some of the microparticles being suspended in the liquid excipient.

According to a further aspect the invention provides a method of treating cancer by brachytherapy, the method comprising the step of implanting a composite material, comprising $^{32}P$ and silicon, as defined in any of the above aspects, into a tumour.

According to a further aspect, the invention provides a method for producing a composite material comprising a volatile element and silicon, the method comprising the steps:

(avi) taking a sample of the volatile element;
(bvi) substantially surrounding the sample of the volatile element with a layer of silicon;
(cvi) applying heat to the silicon in such a manner that a temperature difference is established between at least part of the silicon layer and the sample of the volatile element, and in such a manner that at least some of the volatile element is vaporised; and
(dvi) allowing and/or causing at least some of the volatile element vapour to contact at least part of the layer of silicon in such a manner that a composite material comprising silicon and the volatile element is formed.

The invention will now be described, by way of example only, with reference to the following diagram:

FIG. 1 shows a schematic diagram of a modified furnace for the fabrication, in accordance with the present invention, of a composite material comprising silicon and phosphorus.

(A) FABRICATION OF A COMPOSITE MATERIAL COMPRISING SILICON AND PHOSPHORUS

Two different furnaces were used to perform the invention: a Tilt furnace, not shown in the diagram; and a modified furnace, shown in FIG. 1.

A composite material comprising silicon and phosphorus was produced by heating silicon in a Tilt furnace, and bringing the heated silicon into contact with phosphorus vapour. The Tilt furnace was an induction furnace, having a 35 KW power supply and capacity of around 5 Kg of silicon. Heating was via a graphite susceptor.

The Tilt furnace comprised a number of components including: a melter, a tundish, insulation, a furnace spout, and tundish lid. The melter and tundish each comprised high purity quartz. The insulation, which was located at the top of the furnace, comprised a quartz glass blanket. The furnace spout and tundish lid each comprised alumina and/or silica.

The Tilt furnace was used to combine 4.8 Kg of electronic grade polycrystalline silicon, in a particulate form, and 200 g of pure red phosphorus.

The silicon particles were added to the tundish to form a bed of silicon. The phosphorus (200 g) was then added to the bed and covered with some of the remaining silicon.

The tundish was heated to between 1000 and 1150 C for between 5 to 10 minutes, before increasing the temperature to completely melt the contents of the furnace for between 10 minutes and one hour.

Because of its particulate nature, the volume occupied by silicon is less when molten than when in a solid phase. Once the contents of the furnace start to melt the remainder of the 4.8 Kg of silicon was added.

The resulting silicon and phosphorus alloy was then atomised by standard techniques, using deionised water, to produce a silicon powder, having a phosphorus content of approximately between 1.5 and 2 atomic percent. Impurities such as metallic elements were present, if at all, at levels less than 0.1 atomic percent.

A second, modified, furnace has also been developed, which is shown in FIG. 1. The furnace, comprises a graphite susceptor 1, a quartz crucible 2, a mica sheet 3, a top seal 4, ramming MgO material 5, induction coil with mudding 6, thermocouple 7, quartz window 8, alumina fibre gasket 9, an alumina fibre blanket 11, and a boron nitride plug 13.

The lower portion of the quartz crucible 2 is charged with a layer of silicon particles 12, a tube (not shown in the diagram) is placed onto the surface of the layer of silicon particles 12, and the remainder of the silicon particles 12 are then added to the crucible 2 so that they surround the tube. Phosphorus particles 10 are then added through the tube, in such a way that the top of the phosphorus 10 in the tube is significantly lower than the top of the silicon 12 in the crucible 2. The tube is removed allowing some of the silicon particles 12 to move into some of the volume previously occupied by the tube, thereby covering the phosphorus. In this way the phosphorus 10 is completely surrounded by the silicon 12.

The silicon particles 12 comprise polycrystalline silicon and the phosphorous 10 comprises red phosphorus.

Using the arrangement shown in FIG. 1, the graphite susceptor may be heated to 1100 C in 11 minutes. The increase in temperature causes the silicon 12 and phosphorus 10 to combine, and melt. The melt is then released from the furnace by means of the boron nitride plug and atomised, as described above.

For the absence of doubt, the tilt furnace described in this section is a type of tun furnace.

(B) Generation of $^{32}$P

The composite material comprising silicon and phosphorus in the form of a silicon powder, resulting from the above method described in section (A), was subjected to thermal neutron bombardment in a nuclear reactor to bring about neutron transmutation of the $^{31}$P. The irradiation conditions are chosen to maximise $^{32}$P production within the alloy. Neutron capture results in the formation of $^{32}$P:

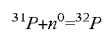

$$^{31}P + n^0 = ^{32}P$$

In this way 2.5 to 10 GBq levels per gram may be obtained which are suitable for treatment of liver cancer tumours of 1 to 3 cm. The amount of $^{32}$P (a radionucleotide) present depends primarily on the amount of P originally present, as well as the neutron flux.

(C) Administration of Radiotherapy Products, According to the Invention, to a Patient Radiotherapy products according to the present invention may have a variety of forms suitable for administration by subcutaneous, intramuscular, intraperitoneal, or epidermal techniques.

The radiotherapy products according to the invention comprise silicon and phosphorus; more specifically they comprise silicon and $^{32}$P. They may be spherical, lozenge shaped, rod shaped, in the form of a strip, or cylindrical. The radiotherapy product may form part of or at least part of: a powder, a suspension, a colloid, an aggregate, and/or a flocculate. The radiotherapy product may comprise an implant or a number of implants, the or each implant comprising silicon and $^{32}$P. Such an implant or implants may be implanted into an organ in which a tumour is located in such a manner as to optimise the therapeutic effect of the $^{32}$P component.

In one aspect of the invention, the method of treatment may involve brachytherapy, and the organ to undergo the brachytherapy may be surgically debulked and the residual space filled with the radiotherapy product. In another aspect the organ to be treated may be cored with an array of needles and the cores back filled with the radiotherapy product of the invention, such a procedure being suitable for brachytherapy of the prostate.

The radiotherapy product may comprise a plurality of silicon microparticles, each particle comprising silicon and phosphorus. The microparticles may be in the form of a silicon powder fabricated by method A, and the phosphorus may comprise $^{32}$P fabricated by method B. The microparticles may be suspended in an excipient such as an excipient comprising a microcellulose and polyethylene glycol formulation. The suspension may then be delivered to the site of the tumour by means of a catheter. This last mentioned method would be suitable for the treatment of cancer, such as liver, pancreatic, or brain cancer, by brachytherapy.

The invention claimed is:

1. A method for producing a composite material comprising phosphorus and silicon, the method comprising the steps:
   (a) taking a sample of phosphorus;
   (b) substantially surrounding the sample of phosphorus with a layer of silicon, the layer of silicon comprising a multiplicity of silicon particles;
   (c) applying heat to the silicon in such a manner that a temperature difference is established between at least part of the silicon layer and the sample of phosphorus, and in such a manner that at least some of the phosphorus is vaporised; and
   (d) allowing and/or causing between 80% and 100% of the phosphorus vapour to contact at least part of the layer of silicon in such a manner that a molten composite material comprising silicon and phosphorus is formed.

2. A method according to claim 1 characterised in that steps (a), (b), and (c) are performed in such a manner that at least part of the silicon layer is heated to a silicon reaction temperature between 900 C and 1500 C.

3. A method according to claim 1 characterised in that the sample of phosphorus comprises red phosphorus.

4. A method according to claim 1 characterised in that method comprises the further step (e) of atomising at least part of the molten composite material generated by step (d).

5. A method according to claim 4 characterised in that the method comprises a further steps: (fi) of cooling and then (fii) porosifying at least some of the composite material formed by step (e).

6. A method according to claim 5 characterised in that the method comprises the further step (g) of irradiating at least some of the composite material produced by (fii) with neutrons in such a manner that at least some of the phosphorus is converted to $^{32}P$.

7. A radiotherpeutic product obtainable by a method according to claim 6.

8. A radiotherapeutic product according to claim 7 for use in the treatment of cancer.

* * * * *